United States Patent [19]
Banks et al.

[11] Patent Number: 5,475,005
[45] Date of Patent: Dec. 12, 1995

[54] BENZIMIDAZOLE ANTHELMINTIC AGENTS

[75] Inventors: Bernard J. Banks, Margate; Christopher J. Dutton, Sandwich, both of United Kingdom; Alexander C. Goudie, Groton, Conn.

[73] Assignee: Pfizer Inc., New York, N.Y.

[21] Appl. No.: 240,652

[22] PCT Filed: Nov. 4, 1992

[86] PCT No.: PCT/EP92/02564

§ 371 Date: May 9, 1994

§ 102(e) Date: May 9, 1994

[87] PCT Pub. No.: WO93/10101

PCT Pub. Date: May 27, 1993

[30] Foreign Application Priority Data

Nov. 12, 1991 [GB] United Kingdom ............... 9124002

[51] Int. Cl.⁶ .................. A61K 31/47; A61K 31/415; C07D 401/04; C07D 235/04
[52] U.S. Cl. .................. 514/307; 546/271; 548/308.7; 548/159; 548/181; 548/207; 548/209; 548/241; 548/309.1; 514/367; 514/370; 514/373; 514/379; 514/395
[58] Field of Search ................. 548/308.7, 159, 548/181, 207, 209, 241, 309.1; 546/271; 514/307, 367, 370, 373, 379, 395

[56] References Cited

U.S. PATENT DOCUMENTS

| | | | |
|---|---|---|---|
| 2,933,502 | 4/1960 | Klopping | 260/299 |
| 3,010,698 | 11/1961 | Loux | 260/309.2 |
| 3,427,388 | 2/1969 | Scoggin | 424/273 |
| 3,574,845 | 4/1971 | Actor et al. | 424/273 |
| 3,915,986 | 10/1975 | Gyurik et al. | 260/309.2 |
| 3,978,217 | 8/1976 | Szöke et al. | 424/245 |
| 4,002,640 | 1/1977 | Beard et al. | 260/309.2 |
| 4,032,536 | 6/1977 | Raeymaekers et al. | 260/309.2 |
| 4,435,418 | 3/1984 | Chow | 424/273 B |
| 4,512,998 | 4/1985 | Nafissi-Varchei | 514/367 |
| 4,826,841 | 5/1989 | Gajewski | 514/237.5 |

FOREIGN PATENT DOCUMENTS

| | | |
|---|---|---|
| 009174A1 | 4/1980 | European Pat. Off. . |
| 387941A1 | 9/1990 | European Pat. Off. . |
| 2046114 | 1/1970 | France . |
| 2425704 | 5/1974 | Germany . |
| 3247615A1 | 7/1984 | Germany . |
| 1123317 | 12/1966 | United Kingdom . |

OTHER PUBLICATIONS

Brown, H. D. et al., "Antiparasitic Drugs. IV. 2–(4'–Thiazolyl)–Benzimidazole, A New Anthelmintic," *JACS*, 83, pp. 1764–1765 (1961).
Ostmann, Orville W. et al., "Parbendazole: A New Anthelmintic For Animals," *Prog. Antimicrob. Anticancer Chemother.*, pp. 159–163, (1980).
Ram, Siya et al., "An Improved Synthesis of Methyl [5–Benzoyl– and 5–p–Fluorobenzoylbenzimidazol–2–yl] Carbamates," *Org. Prep. Proced. Int.*, 17, No. 3, pp. 215–218 (1985).
Sharma, Satyavan et al., "The Benzimidazole Anthelmintics–Chemistry and Biological Activity," *Proc. Drug Res.*, pp. 85–161 (1983).
Averkin, E. A. et al., "Methyl 5(6)–Phenylsulfinyl–2–benzimidazolecarbamate, a New, Potent Anthelmintic," *Journal of Medical Chemistry*, 18, No. 11, pp. 1164–1166 (1975).
Hoff, D. R. et al., "A New Broad–Spectrum Anthelmintic: 2–(4–Thiazolyl)–5–isopropoxycarbonylamino–benzimidazole," *Experientia* 26/5, pp. 550–551 (1970).
Raeymaekers, A. H. M. et al., "Synthesis and Anthelminthic Activity of Alkyl–(5–acyl–1–H–benzimidazol–2–yl) Carbamates," *Drug Res.*, 28, pp. 586–594 (1978).
Rajappa, Srinivasachjari, "Benzimidazoles, Processes for Their Preparation and Pharmaceutical Preparations Containing Such Compounds," *Patent Journal*, p. 134, Jun. 1980.
Kruse, Lawrence I. et al., *J. Med. Chem.*, 32, No. 2, pp. 409–417 (1989).
Chemical Abstracts, 94, No. 13, 30 Mar. 1981, (Columbus, Ohio, US), see p. 747, column 2, abstract No. 103370r, & ZA, A 7902975 (Ciba–Geigy AG) 25 Jun. 1980.
Chemical Abstracts, 107, No. 9, 1987, (Columbus, Ohio, US), T. Ravindranathan et al.: "Synthesis of mebendazole and enviroxime. Acylation of 2–amino–5–benzoybenzimidazole", see p. 695, abstract No. 77698u, & Org. Prep. Proced. Int. 1987, 19(1), 9–16, see abstract.
International Search Report and two–page annex in corresponding application No. PCT/EP 92/02564 May 2, 1993.

*Primary Examiner*—Johann Richter
*Assistant Examiner*—Laura L. Stockton
*Attorney, Agent, or Firm*—Peter C. Richardson; Gezina Holtrust; B. Timothy Creagan

[57] ABSTRACT

Benzimidazole anthelmintic agents of the formula (I) and their non-toxic salts, wherein $R^1$, which is in the 5(6)-position, is either H or certain stated substituents, "alk" is a methylene or ethylene group; $R^2$ is cyano, $C_1$–$C_4$alkenyl, $C_2$–$C_4$ alkynyl, $C_2$–$C_4$alkanoyl, $C_1$–$C_4$alkoxy, $C_2$–$C_4$alkenoxy, aryl, heteroaryl, aryl-($C_1$–$C_4$alkoxy) or heteroaryl-($C_1$–$C_4$alkoxy), in which "aryl" means phenyl optionally substituted by 1 to 3 substituents each independently selected from halo, $C_1$–$C_4$alkyl, $C_1$–$C_4$alkoxy, $C_1$–$C_4$alkylthio, $C_1$–$C_4$alkylsulphinyl, and $C_1C_4$alkylsulphonyl in which "heteroaryl" means thienyl, furyl or pyridininyl all optionally substituted by 1 to 3 substituents each independently selected from halo, $C_1$–$C_4$alkyl, $C_1$–$C_4$alkoxy, $C_1$–$C_4$alkylthio, $C_1$–$C_4$alkylsulphinyl and $C_1$–$C_4$alkylsulphonyl; and $R_3$ is a $C_1$–$C_4$alkyl group. The anthelmintic agents (I) are, unexpectedly, active topically and parenterally, and are thus suitable for spot-on, pour-on, or parental (especially intramuscular) administration.

10 Claims, No Drawings

BENZIMIDAZOLE ANTHELMINTIC AGENTS

This application is a 371 of PCT/EP92/02564 filed Nov. 4, 1992.

The present invention related to certain benzimidazole anthelmintic agents which, quite unexpectedly, are topically and parenterally active and are thus suitable for transdermal and parenteral (especially intramuscular) administration.

These benzimidazole derivatives are represented by the formula:

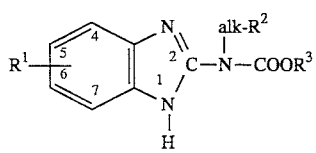
(I)

and their non-toxic salts, wherein $R^1$, which is in the 5(6)-position, is either (i) H, benzoyl, phenyloxy, phenylthio, phenylsulfinyl, phenylsulfonyl, phenylsulfonyloxy, $C_1$–$C_6$ alkyl, $C_1$–$C_6$ alkoxy, $C_1$–$C_6$ alkylthio, $C_1$–$C_6$ alkylsulfinyl, $C_1$–$C_6$ alkylsulfonyl or ($C_3$–$C_7$ cycloalkyl) carbonyl, said phenyl groups, and the phenyl portion of said benzoyl group, optionally having 1 to 3 substituents each independently selected from halo, $C_1$–$C_4$ alkyl, halo-($C_1$–$C_4$ alkyl), $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkanoyl, nitro, isothiocyanato, and cyano; or (ii) a group of the formula:

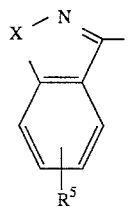

where X is O,S,SO,$SO_2$ or $NR^4$ in which $R_4$ is hydrogen, $C_1$–$C_4$ alkyl, phenyl or phenyl-($C_1$–$C_4$ alkyl), wherein said phenyl and the phenyl portion of said phenyl-($C_1$–$C_4$) alkyl) groups are optionally substituted by 1 or 2 substituents each selected from $C_1$–$C_4$ alkyl, halo, hydroxy and $C_1$–$C_4$ alkoxy; and $R_5$ is H, $C_1$–$C_4$ alkyl, halo, hydroxy or $C_1$–$C_4$ alkoxy;

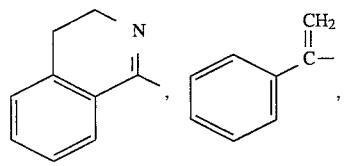

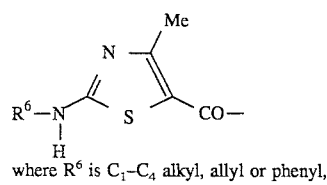

where $R^6$ is $C_1$–$C_4$ alkyl, allyl or phenyl,

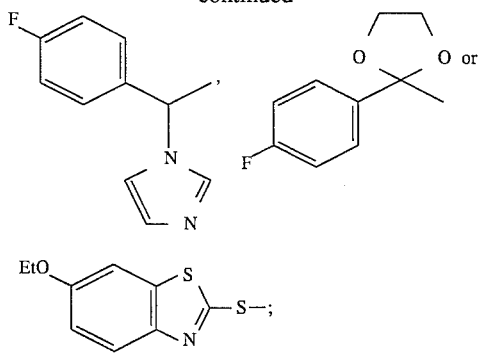

"alk" is a methylene or ethylene group; $R^2$ is cyano, $C_2$–$C_4$ alkenyl, $C_2$–$C_4$ alkynyl, $C_2$–$C_4$ alkanoyl, $C_1$–$C_4$ alkoxy, $C_2$–$C_4$ alkenoxy, aryl, heteroaryl, aryl-($C_1$–$C_4$ alkoxy) or heteroaryl-($C_1$–$C_4$ alkoxy), in which "aryl" means phenyl optionally substituted by 1 to 3 substituents each independently selected from halo, $C_1$–$C_4$ alkyl, $C_1$–$C_4$ alkoxy, $C_1$–$C_4$ alkylthio, $C_1$–$C_4$ alkylsulphinyl and $C_1$–$C_4$ alkylsulphonyl, and in which "heteroaryl" means thienyl, furyl or pyridinyl all optionally substituted by 1 to 3 substituents each independently selected from halo, $C_1$–$C_4$ alkyl, $C_1$–$C_4$ alkoxy, $C_1$–$C_4$ alkylthio, $C_1$–$C_4$ alkylsulphinyl and $C_1$–$C_4$ alkylsulphonyl; and $R_3$ is a $C_1$–$C_4$ alkyl group.

Preferred alkyl and alkoxy groups have 1 to 4 carbon atoms.

$R^1$ is preferably H, $C_1$–$C_4$ alkyl, $C_1$–$C_4$ alkoxy, $C_1$–$C_4$ alkylthio, $C_1$–$C_4$ alkylsulphinyl, phenylthio, phenylsulfinyl, benzoyl optionally substituted by halo, phenylsulfonyloxy optionally substituted by halo, or 1,2-benzisoxazol-3-yl.

More preferably, $R^1$ is H, benzoyl, 4-fluorobenzoyl, 4-fluorophenylsulfonyloxy, n-propylthio, n-propylsulfinyl, phenylthio, phenylsulfinyl, n-butyl, n-propyloxy, or 1,2-benzisoxazol-3-yl.

Most preferably, $R^1$ is n-propylthio;

"alk" is preferably methylene.

$R^2$ is preferably methoxy, ethoxy, allyloxy, benzyloxy, phenyl optionally substituted by 1 to 3 methoxy substituents, cyano, ethynyl, vinyl or acetyl.

$R^3$ is preferably methyl.

Alkyl, alkoxy, alkenyl and alkynyl groups, when appropriate, can be straight or branched chain. "Halo" means F, Cl, Br or I.

Suitable non-toxic acid addition salts, suitable for veterinary use, are for example the hydrochloride, hydrobromide, and sulphate salts. These can all be prepared conventionally.

The benzimidazoles of the formula (I) and their salts are in particular anthelmintics suitable for the control of parasitic diseases in both human and non-human animals such as sheep and cattle and domestic pets. The compounds exhibit activity against mature and immature parasitic forms of, for example, nematodes, trematodes and cestodes such as are represented by Trichostrongylus, Dictyocaulus, Ostertagia, Nematodirus, Stronglyoides, Trichuris, Haemonchus, Cooperia, Dirofilaria, Toxocara, Trichuris, Fasciola and *Monezia* species.

Efficient control of these species is achieved by introducing into said animals circulatory system an anthelmintically-effective amount of a compound (I) or salt thereof. In the case of these compounds, it has been unexpectedly found that this control can be achieved by percutaneous absorption and/or penetration from a liquid or cream formulation applied directly to the animals' skin. Such liquid formulations are known as "pour-on formulations". Such pour-on formulations are characterised in that the active ingredient, i.e. the compound (I) or salt thereof, is dissolved, emulsified or suspended in a suitable solvent or solvent mixture which is tolerable by the skin and non-toxic to the animal, optionally with certain auxiliary ingredients.

To prepare pour-on formulations, the compounds of the formula (I) and their salts are formulated in a conventional manner by mixing them with carriers which are effective in penetrating the skin, the compound (I) then being absorbed by the animal through the skin and transmitted systemically throughout the animal.

The pour on formulation contains:

1. a non volatile drug solvent or solvent mixture which may include solvents normally classed as transdermal penetration enhancers, and, optionally, one or more of the following:
2. a solvent with the specific role of enhancing transdermal penetration if such a solvent is not already present performing function 1 as the main drug solvent;
3. an accessory spreading agent if this auxiliary function is not performed adequately by the drug solvent (1) and any transdermal penetration enhancer (2);
4. a volatile solvent. This volatile solvent may aid the spreading and distribution of components 1 and 2, adjust the formulation to a convenient dosing volume, and ensure solubility and miscibility of the formulation in extreme storage conditions; and
5. further adjuvants, where necessary; to ensure chemical stability in storage and use, to increase the viscosity of the formulation to prevent run off, to deter other animals from licking the composition off the treated animal, and to protect the skin from undesirable irritation.

Suitable drug solvents (1) are selected to achieve adequate solubility from:

| | |
|---|---|
| Spreading oils - | silicone oils, isopropyl myristate, isopropyl palmitate, caprylic/capric acid triglyceride, saturated triglycerides of naturally occuring fatty acids, fatty acid esters (e.g. ethyl oleate), and fatty acid esters which correspond to synthetic anatine uropygial gland fat. |
| Aliphatic hydrocarbons - | e.g. light paraffin oil. |
| Hydroxylic solvents - | less volatile alcohols (e.g. hexanol, octanol), propylene glycol, polypropylene glycols, ethylene glycol, diethylene glycol, glycerols and ether and or ester substituents of these solvents, (e.g. Triacetin), benzyl alcohol and carboxylic acid esters (e.g. benzyl benzoate), butyl acetate, propylene carbonate and ethyl lactate. |
| Polyalkoxylated solvents - | Polyethylene glycols, polyglycol ethers and or esters e.g. 2-(2-alkoxy)ethoxyethanols and 2-(2-alkoxy)ethoxyethyl alkanoates. |
| Vegetable oils - | not included in the definition of spreading oils e.g. corn, sesame, olive, pine, linseed, cottonseed and ground nut oil. |
| Penetration enhancing agents (2) - | (a) e.g. dimethylsulphoxide, dimethylformamide and dimethylacetamide; (b) Pyrrolidones. In particular 2-pyrrolidone, N-methylpyrrolidone, and 1 or 5 and 1,5 alkyl substituted pyrrolidones e.g. 1,5-dimethyl-2-pyrrolidone or carboxylic acid substituted pyrrolidones; (c) alkylsulphoxides, sugar esters and phosphine oxides; and (d) azacycloalkan-2-ones. |

While these solvents may be used in miscible combinations, miscibility may be achieved by incorporation of a ternary solvent, if required, to provide adequate drug solubility.

Accessory spreading agents (3) comprising spreading oils (if these are not used as the main drug solvent as previously listed in (1)) or surface active agents where the term surface active agent is used to cover materials variously called wetting agents, emulsifying agents and dispersing agents. These include:

Non-ionic water soluble emulsifiers such as alkylaryl polyglycol ethers, polyoxyethylene alkylaryl ether, alkylpolyglycol ethers, polyoxyethylene esters and ethers, polyoxyethylene sorbitan mono fatty acid esters, sorbitan mono fatty acid esters, ethoxylated nonyl phenols, isooctylphenol, polyethoxyethanol and polyethoxylated castor oil (Cremophor EL$^R$). Anionic surfactants including soaps, fatty sulphate esters (e.g. dodecyl Na sulphate) fatty aromatic sulphonates (e.g. alkylbenzenesulphonates) more complex fatty sulphonates such as the amide condensation product of oleic acid and N-methyltaurine, the sodium sulphonate of dioctylsuccinate and the disodium ethoxylated nonylphenol half ester of sulphosuccinic acid. Cationic agents such as cetyltrimethylammonium bromide may also be used as well as ampholytic surfactants such as di-Na-N-lauryl betaiminodiopropionate or lecithin.

Suitable volatile solvents (4) include:

Ketones such as acetone, methyl ethyl ketone, methyl isobutyl ketone and cyclohexanone; simple alcohols (in particular methanol, ethanol and [especially] isopropylalcohol); straight and branched alkylethers (e.g. dibutyl diisopropyl ether), tetrahydrofuran, glycol ethers and straight and branched chain alkyl acetates (e.g. isopropyl acetate) and other esters such as lactic acid ethyl ester; aromatic hydrocarbons such as xylene, benzene, toluene, alkylnaphthalenes and chlorobenzenes; and aliphatic hydrocarbons such as paraffins of chain length 6–20 and halogenated aliphatic hydrocarbons.

Appropriate auxiliary additives (5) include:

| | |
|---|---|
| Stability enhancers - | antioxidants e.g. ascorbic acid, butylated hydroxyanisole and butylated hydroxytoluene. |
| Colourants - | inorganic pigments, iron (II) oxide, titanium dioxide, Prussian blue; organic dyestuffs e.g. alizarin based, azo dye- |

| | -continued |
|---|---|
| | based or metal phthalocyanine-based dyestuffs. |
| Adhesion promoters - | carboxymethylcellulose, methylcellulose and other cellulose and starch derivatives, polyacrylates, alginates, gelatines, gum arabic, polyvinylpyrrolidone, copolymers of methylvinyl ether and maleic anhydride, polyethylene glycols, paraffins, oils and waxes, hydrogenated castor oil, lecithins and synthetic phospholipids. |
| Oral deterrents - | such as bitter aloes. |
| Emolients - | such as lanolin. |

The drug is dissolved in typical formulations which contain 1–100% of the main drug solvents, usually not more than 70% and ideally not more than 20%. The rest of the formulation is composed in the main by the volatile solvent which may comprise 0–99% of the formulation and preferably not less than 30%. Further transdermal penetration enhancers (0–33%), accessory spreading agents (0–25%) and adjuvants (0–5%) are added as required.

Preferred formulations for the actives were selected from typical formulations.

| Ingredient | % Composition |
|---|---|
| Formulation 1 | |
| 2-(2-Butoxyethoxy)ethanol | 100 |
| Formulation 2 | |
| 2-(2-Butoxyethoxy)ethanol | 5 |
| Propan-2-ol | 95 |
| Formulation 3 | |
| Ethyl oleate | 50 |
| Isopropyl acetate | 50 |
| Formulation 4 | |
| Dimethylsulphoxide | 20 |
| Xylene | 80 |
| Formulation 5 | |
| Cetyl 2-ethylhexanoate/ stearyl 2-ethylhexanoate blend | 10 |
| Propan-2-ol | 90 |
| Formulation 6 | |
| PEG 300 | 60 |
| iso-octylphenoxypolyethoxyethanol e.g. Triton X-100 ® | 10 |
| Propan-2-ol | 30 |
| Formulation 7 | |
| Propylene glycol | 50 |
| Hydroxypropyl cellulose (MW 1 × 10$^6$ Dalton) e.g. Klucel HPC HF ® | 0.5 |
| Butylated hydroxyanisole | 0.02%w/v |
| Ethanol | to 100% |
| Formulation 8 | |
| Propylene glycol | 5 |
| Sodium Erythrosine | 0–0.01%w/v |
| Methanol | to 100% |
| Formulation 9 | |
| Triacetin | 60 |
| Isopropyl acetate | 40 |

The pour-on formulations typically contain the active compound (I) salt thereof in an amount of from 0.5% wt/vol to 60% wt/vol. A typical pour-on formulation would contain 1 to 50 mg of the active ingredient per kg of animal body weight in, say, 0.01–1 ml per kg body weight of the animal. Typically the formulation is simply poured on the animal. Concentrated formulations are often referred to as "spot-on" formulations, which are spotted onto the animal.

The compounds of formula (I) are administered as a formulation appropriate to the specific use envisaged and to the particular species of host animal being treated and the parasite involved. For use as an anthelmintic the compounds may be administered orally in the form of a capsule, bolus, tablet or drench or as a pour-on formulation, or alternatively, they can be administered by injection (e.g. subcutaneously, intramuscularly or intravenously) or as an implant. Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from 0.5 to 60% by weight of the active ingredient. These formulations will vary with regard to the weight of active compound depending on the species of host animal to be treated, the severity and type of infection and the body weight of the host. For parenteral and oral administration, typical dose ranges of the active ingredient are 1–50 mg per kg of body weight of the animal. Pour-on formulations have been previously described.

As an alternative the compounds may be administered with the animal feedstuff and for this purpose a concentrated feed additive or premix may be prepared for mixing with the normal animal feed.

The compounds of the invention are highly active antiparasitic agents having utility not only as anthelmintics, but as ectoparasiticides, insecticides, acaricides, and antifungal agents and antiprotozoal agents.

Thus the compounds are effective in treating a variety of conditions caused by endoparasites including, in particular, helminthiasis which is most frequently caused by a group of parasitic worms described as nematodes, cestodes and trematodes, and which can cause severe economic losses in swine, sheep, horses and cattle as well as affecting domestic animals and poultry. The compounds are also effective against other nematodes which affect various species of animals including, for example, Dirofilaria, Toxocara, Ancyclostoma, Dipylidium, Echinococcus and Taenia in dogs and various parasites which can infect humans including gastrointestinal parasites such as Ancylostoma, Necator, Ascaris, Strongyloides, Trichinella, Capillaria, Trichuris, Enterobius and parasites which are found in the blood or other tissues and organs such as filarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against arthropod pests of stored grain and of agricultural plants such as spider mites, aphids, caterpillars and against migratory orthopterans such as locusts.

For use as an insecticide and for treating agricultural pests the compounds are applied as sprays, dusts, emulsions and the like in accordance with standard agricultural practice.

The compounds of the formula (I) can be prepared by alkylating an optionally protected 5-(6) benzimidazole of the formula:

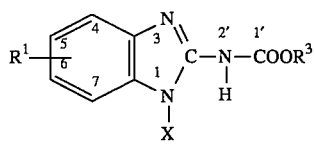
(II)

where $R^1$ is in the 5-(6-) position, $R^1$ being as defined for formula (I), and X is H or an amino-protecting group, with an alkylating agent of the formula:

$R^2$-alk-Q  (III)

where Q is a suitable leaving group, such as chloro, bromo or iodo, and alk and $R^2$ are as defined for formula (I).

The novel compounds (II) in which X is an amino-protecting group also form a part of the invention.

A preferred amino-protecting group is t-butoxycarbonyl.

The reaction is preferably carried out in the presence of a base such as potassium carbonate. The reaction is typically carried out in an organic solvent such as dimethylformamide at about room temperature. The amino-protecting group X, if present, is then removed conventionally: for example t-butoxycarbonyl is typically removed by treatment with trifluoroacetic acid at about room temperature.

Because in the benzimidazole end products (I) and starting materials (II), the position of the hydrogen atom at the nitrogen atom of the imidazole ring cannot be determined (tautomerism), it will be appreciated that the compounds are correctly named as 5(6)-substituted benzimidazoles.

The starting materials (II) in which X is an amino-protecting group are preparable by the N-protection of the corresponding benzimidazoles having a hydrogen atom at the 1-position with a suitable reagent, e.g. di-t-butyldicarbonate. These "unprotected" benzimidazoles are known compounds and in many cases have generic non-proprietary names, as follows:

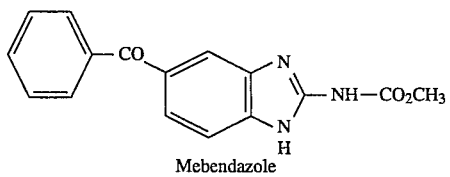
Mebendazole

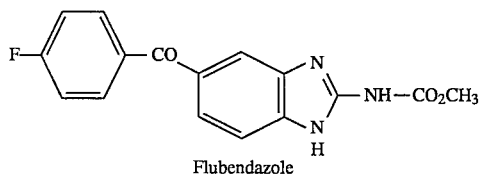
Flubendazole

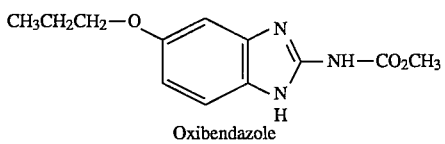
Oxibendazole

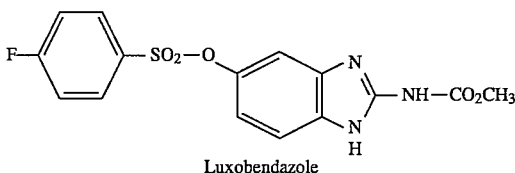
Luxobendazole

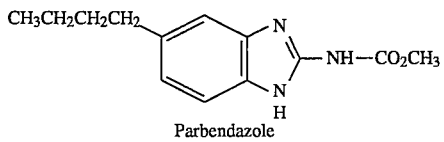
Parbendazole

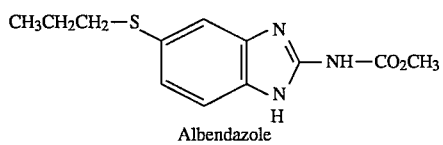
Albendazole

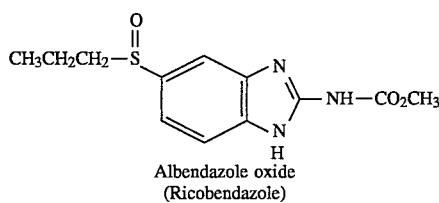
Albendazole oxide
(Ricobendazole)

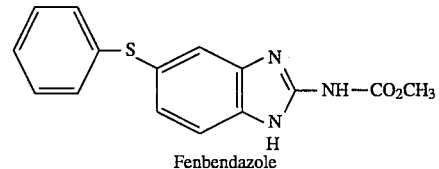
Fenbendazole

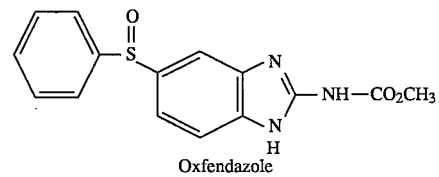
Oxfendazole

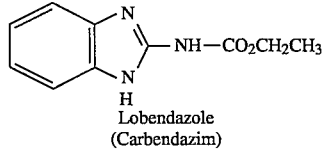
Lobendazole
(Carbendazim)

For further details of these compounds please also see for example the following references:

S. Sharma et.al., Proc. Drug. Res., 1983, 27, 85;
O. W. Ostmann et.al., Prog. Antimicrob. Anticancer Chemother, 1969, 1, 159;
A. H. M. Raeymaekers, Arzneim-Forsch/Drug. Res., 28(1), 586;
E. A. Averkin et.al., J.Med.Chem, 1975, 18, 1164;
S. Ram et.al., Org. Prep. Proced. Int, 1985, 17, 215;
H. D. Brown et.al., JACS, 1961, 83, 1764;
D. R. Hoff et.al., Experientia, 1970, 26, 550;

U.S. Pat. No. 3,010,968, GB 1123317; U.S. Pat. No. 3,915,986; U.S. Pat. No. 4,002,640; U.S. Pat. No. 4,435,418; U.S. Pat. No. 4,826,841; U.S. Pat. No. 4,032,5361; U.S. Pat. No. 4,512,998; DE-A-3247615; EP-A-0387941; EP-A-0009174; and ZA-7902975.

$C_1$–$C_6$ Alkylthio groups represented by $R^1$, or present in $R^2$, can be oxidized to $C_1$–$C_6$ alkylsulfinyl or alkylsulfonyl groups by conventional techniques, e.g. by the use of 1 or more equivalents of m-chloroperbenzoic acid, as appropriate, in a suitable solvent such as methylene chloride.

The utility of the compounds as anthelmintics when given transdermally can, for example, be assessed by the following technique:

Male Cobb-Wistar rats weighing 40–50 g (3–4 weeks old) are used. The animals are fed on normal cubed rodent diet containing 60 ppm of the immunosuppressant hydrocortisone acetate. Immunosuppression commences one week prior to infection and is maintained until necropsy. Both food and water are given ad lib.

Each rat is given 1500 *T.colubriformis* infective larvae orally. Ovine-derived larvae are prepared from stock cultures immediately before dosing and checked microscopically for viability. Only motile, viable larvae are used. Parasites are administered in 0.25 ml of water.

One to three weeks post-infection animals are randomly assigned to either treatment (generally 5 rats) or control (generally 10 rats) groups. Solutions of test compounds in appropriate vehicles (see below) are administered topically by pipette to a shaven area (approximately 1 square inch) of the back close to the neck. Drug concentrations in the vehicle are adjusted such that each animal receives the desired dosage in < 0.25 ml/100 g body weight. At the time of dosing the weight of the animals ranges from 90 to 110 g. All animals are necropsied three days post-dosing.

At necropsy the small intestine of each animal is removed and placed in a plastic pot containing 20 ml of pepsin digest mixture, comprising pepsin A powder 8 g, NaCl 8.5 g, plus 16 ml concentrated HCl in 1 L of distilled water. The digests are incubated at 37° C. for 4 hours prior to washing over a 75 um sieve with a high pressure water spray. Worms retained on the sieve are collected by washing into fresh pots and stained using an iodine/potassium iodide solution comprising iodine 30 g, potassium iodide 40 g, plus 30 ml methylated spirits in 70 ml distilled water. The contents of each pot is then diluted to a final volume of 500 ml with distilled water and a 50 ml aliquot taken for worm counting. The efficacy of each drug treatment is determined as the percent reduction from the average worm burden of untreated controls.

The following Examples illustrate the preparation of the compounds of the formula (I). The Preparation illustrates the preparation of a starting material.

PREPARATION 1

Preparation of 2-(methoxycarbonylamino)-1-(t-butoxycarbonyl)-(5- and 6-n-propylthio)benzimidazole To a stirred suspension of methyl 5(6)-n-propylthiobenzimidazole- 2-carbamate(albendazole) (150 g, 0.57 M) in 2L of tetrahydrofuran was added 123 g (0.57 M) of di-t-butyl dicarbonate. The mixture was stirred for 18 hours at room temperature and then for 5.5 hours at 50° C. A further 62 g of di-t-butyl dicarbonate in 150 ml of tetrahydrofuran was then added. The mixture was stirred for 18 hours at room temperature then for a further 2 hours at 50° C. After evaporation, the residue was slurried with diethyl ether (1 L) and filtered. The filtrate was evaporated and crystallized from n-hexane to yield 66 g of a mixture of the title compounds. The filter cake was slurried with methylene chloride, filtered and the filtrate and the filtrate was evaporated. The residue was crystallized from n-hexane to yield a further 61 g of the title compounds.

| Analysis | |
| --- | --- |
| Found: | C, 55.91%; H, 6.41%; N, 11.58%. |
| $C_{17}H_{23}N_3O_4S$ requires | C, 55.87%; H, 6.34%; N, 11.50%. |
| M.Pt. 85–87° C. | |

EXAMPLE 1

Preparation of 2-[(N-methoxycarbonyl-N-methoxymethyl)-amino]-[5C6)-n-propylthio]benzimidazole 7.3 g (0.02 M) of 2-(methoxycarbonylamino)-1-(t-butoxycarbonyl)-( 5- and 6-n-propylthio)benzimidazole, 1.5 ml (0.02 M) of chloromethyl methyl ether, 5.6 g (0.04 M) of anhydrous potassium carbonate and 50 ml of dimethylformamide were stirred together at room temperature for 72 hours then evaporated to dryness.

The residue was dissolved in ethyl acetate and washed with water, saturated brine and then dried over magnesium sulphate. The mixture was filtered and the filtrate was evaporated. To the residue was added 20 ml of trifluoroacetic acid and the mixture was stirred at room temperature for 2 hours then neutralized with solid potassium bicarbonate. The mixture was then dissolved in ethyl acetate, washed with water and brined then dried over magnesium sulphate, filtered and evaporated. The product was purified by chromatography on silica, eluting with 1% methanol in methylene chloride. The relevant fractions were combined and evaporated then the residue was crystallized from ether and hexane to yield 1.5 g of the title compound.

| Analysis | |
| --- | --- |
| Found: | C, 54.89%; H, 6.12%; N, 13.69%. |
| $C_{14}H_{19}N_3O_3S$ requires | C, 54.35%; H, 6.19%; N, 13.58%. |
| M.Pt. 62° C. | |

EXAMPLE 2

Preparation of 2-[(N-methoxycarbonyl-N-ethoxymethyl)amino]-[5(6)-n-propylthio]benzimidazole The procedure of Example 1 was repeated using chloromethyl ethyl ether in place of chloromethyl methyl ether.

| Analysis | |
| --- | --- |
| Found: | C, 55.98%; H, 6.56%; N, 13.09%. |
| $C_{15}H_{21}N_3O_3S$ requires | C, 55.71%; H, 6.54%; N, 12.99%. |
| Mt.Pt. 59–63° C. | |

EXAMPLE 3

Preparation of
2-[(N-methoxycarbonyl-N-allyloxymethyl)
amino]-[5(6)-n-propylthio]benzimidazole The procedure of Example 1 was repeated using chloromethyl allyl ether (see Hurd et.al., JACS, 74, 128, 1952) in place of chloromethyl methyl ether. The product was an oil.

NMR; H (ppm, CDCl$_3$, 300 MHz) 1.0 (3H,t), 1.65 (2H,dt), 2.85 (2H,t), 3.9 (3H,s), 4.2–6.0 (5H,m), 5.3 (2H,s), 7.5 (3H,m), 11.0 (1H,br s).

EXAMPLE 4

Preparation of
2-[(N-methoxycarbonyl-N-benzyloxymethyl)
amino]-[5(6)-n-propylthio]benzimidazole The procedure of Example 1 was repeated using chloromethyl benzyl ether in place of chloromethyl methyl ether.

| Analysis | |
| --- | --- |
| Found: | C, 61.96%; H, 5.95%; N, 10.67%. |
| C$_{20}$H$_{23}$N$_3$O$_3$S requires: | C, 62.32%; H, 6.01%, N, 10.90%. |
| M.Pt: 59–63° C. | |

EXAMPLE 5

Preparation of
2-[N-methoxycarbonyl-N-3,4,5-trimethoxybenzyl)
amino]-[5(6)n-propylthio]benzimidazole The procedure of Example 1 was repeated using 3,4,5-trimethoxybenzyl chloride in place of chloromethyl methyl ether.

| Analysis | |
| --- | --- |
| Found: | C, 59.67%; H, 6.08%, N, 9.72%. |
| C$_{22}$H$_{27}$N$_3$O$_5$S requires: | C, 59.31%; H, 6.11%, N, 9.43%. |
| M.Pt: 133–136° C. | |

EXAMPLE 6

Preparation of
2-[(N-methoxycarbonyl-N-cyanomethyl)amino]-
[5(6)-n-propylthio]benzimidazole A mixture of methyl 5(6)-n-propylthiobenzimidazole (2,65 g, 0.01M), iodoacetonitrile (1,67 g, 0.01M), potassium carbonate (3 g, 0.22 M) and dimethylformamide (30 ml) was stirred at room temperature for two days, after which the solvent was evaporated. The residue was partitioned between ethyl acetate and water. The aqueous layer was separated and re-extracted with ethyl acetate. The combined organic layers were washed with water, dried (MgSO$_4$) and evaporated. The crude product was purified by column chromatography on silica gel ("Silica Gel 60", Merck [Trade Mark], 100 g) eluting initially with dichloromethane and then with dichloromethane containing 1% methanol. Combination and evaporation of appropriate fractions gave 2-[(N-methoxycarbonyl-N-cyanomethyl) amino]-[5(6)-n- propylthio] benzimidazole (1.46 g, 48%).

| Analysis | |
| --- | --- |
| Found: | C, 55.31%; H, 5.01%, N, 18.12%. |
| C$_{14}$H$_{16}$N$_4$O$_2$S requires: | C, 55.25%, H, 5.30%; N, 18.41%. |
| M.Pt: 151–152° C. | |

EXAMPLE 7

Preparation of 2-[(N-methoxycarbonyl-N-propargyl)
amino]-[5(6)-n-propylthio]benzimidazole The procedure of Example 6 was repeated using propargyl bromide in place of iodoacetonitrile.

| Analysis | |
| --- | --- |
| Found: | C, 59.21%; H, 5.54%, N, 13.76%. |
| C$_{15}$H$_{17}$N$_3$O$_2$S requires: | C. 59.39%; H, 5.65%; N, 13.85%. |
| M.Pt: 127–128° C. | |

EXAMPLE 8

Preparation of
2-[(N-methoxycarbonyl-N-allyl)amino]-
[5(6)-n-propylthio]benzimidazole The procedure of Example 6 was repeated using allyl bromide in place of iodoacetonitrile.

| Analysis | |
| --- | --- |
| Found: | C, 59.29%; H, 6.22%; N, 13.74%. |
| C$_{15}$H$_{19}$N$_3$O$_2$S requires: | C. 58.99%; H, 6.27%; N, 13.76%. |
| M.Pt: 85–87° C. | |

EXAMPLE 9

Preparation of
2-[{N-methoxycarbonyl-N-(2-oxopropyl)}
amino]-[5(6)-n-propylthio]benzimidazole The procedure of Example 6 was repeated using chloroacetone in place of iodoacetonitrile.

NMR; $_H$ (ppm, CHCl$_3$, 300 MHz)= 1.0 (3H,t), 1.65 (2H,dt), 2.62 (3H,s), 2.88 (2H,t), 3.9 (3H,s), 5.05 (2H,s), 7.25–7.7 (3H,m), 11.0 (1H,brs).

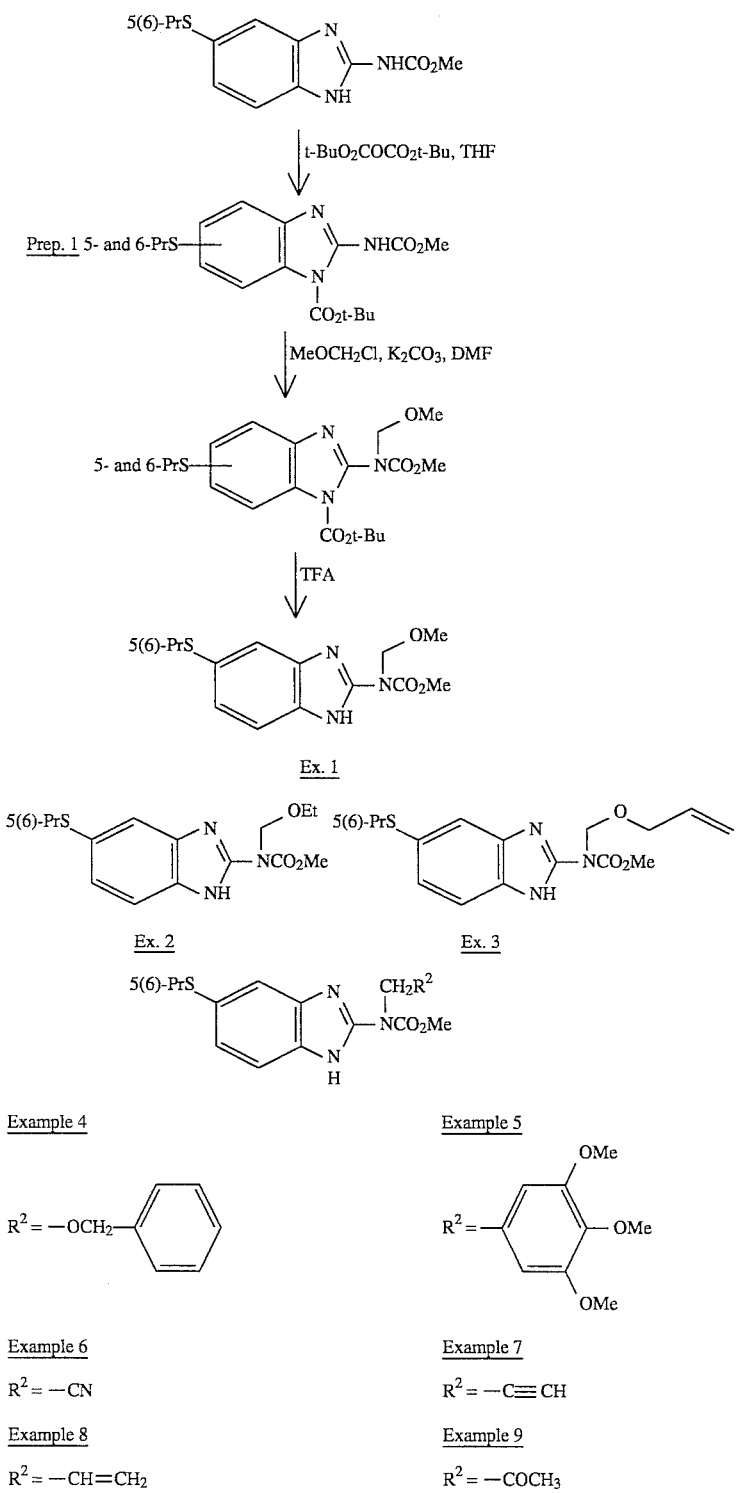

Example 4  
$R^2 = -OCH_2-$phenyl

Example 5  
$R^2 = $ 3,4,5-trimethoxyphenyl (OMe, OMe, OMe)

Example 6  
$R^2 = -CN$

Example 7  
$R^2 = -C\equiv CH$

Example 8  
$R^2 = -CH=CH_2$

Example 9  
$R^2 = -COCH_3$

EXAMPLE 10

A composition suitable for transdermal administration is as follows:

| | |
|---|---|
| 2-[N-(methoxycarbonyl)-N-(methoxy-methyl)amino]-[5(6)-propylthio]benzimidazole (Product of Example 1) | 21 g |
| Butyl digol[2-(2-butoxyethoxy) ethanol] } Equal proportions fheightfwidth | 24.5 g |

-continued

| 2-Pyrrolidone | by volume | 28.8 g |
| Isopropylacetate | | 22.4 g |
| | | 96.7 g |

EXAMPLE 11

A composition suitable for parenteral administration is as follows:

| 2-[N-(methoxycarbonyl)-N-(methoxymethyl)amino]-[5(6)-propylthio]benzimidazole (Product of Example 1) | 21 g |
| Benzyl benzoate | 0.0063 g |
| Sesame oil | 0.7312 g |
| | 0.9609 g |

We claim:

1. A benzimidazole derivative of the formula:

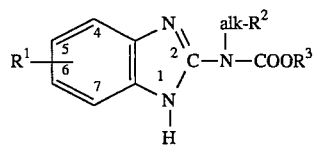

or a non-toxic salt thereof, wherein $R^1$, which is in the 5(6)-position, is either (i) H, benzoyl, phenyloxy, phenylthio, phenylsulfinyl, phenylsulfonyl, phenylsulfonyloxy, $C_1-C_6$ alkyl, $C_1-C_6$ alkoxy, $C_1-C_6$ alkylthio, $C_1-C_6$ alkylsulfinyl, $C_1-C_6$ alkylsulfonyl or $(C_3-C_7$ cycloalkyl) carbonyl, said phenyl groups, and the phenyl portion of said benzoyl group, optionally having 1 to 3 substituents each independently selected from halo, $C_1-C_4$ alkyl, halo-$(C_1-C_4$ alkyl), $C_1-C_4$ alkoxy, $C_1-C_4$ alkylthio, $C_1-C_4$ alkylsulfinyl, $C_1-C_4$ alkylsulfonyl, $C_2-C_4$ alkanoyl, nitro, isothiocyanato, and cyano; (ii) a group of the formula:

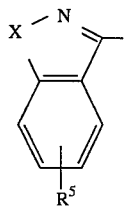

where X is O, S, SO, $SO_2$ or $NR^4$ in which $R_4$ is hydrogen; $C_1-C_4$ alkyl, phenyl or phenyl-$(C_1-C_4$ alkyl), wherein said phenyl and the phenyl portion of said phenyl-$(C_1-C_4)$ alkyl) groups are optionally substituted by 1 or 2 substituents each selected from $C_1-C_4$ alkyl, halo, hydroxy and $C_1-C_4$ alkoxy; and $R_5$ is H, $C_1-C_4$ alkyl, halo, hydroxy or $C_1-C_4$ alkoxy; or (iii) a group of the formula:

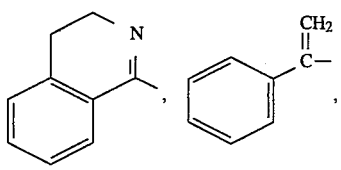

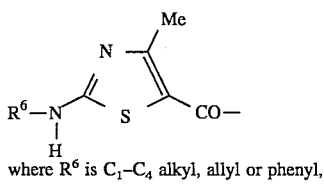

where $R^6$ is $C_1-C_4$ alkyl, allyl or phenyl,

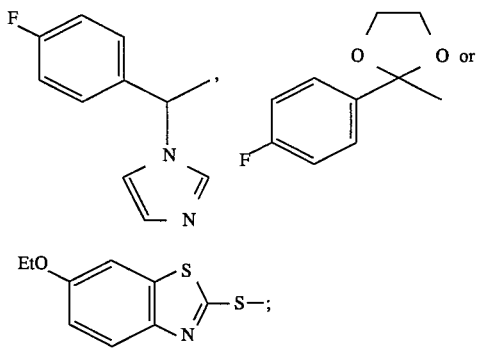

"alk" is a methylene or ethylene group; $R^2$ is cyano, $C_2-C_4$ alkenyl, $C_2-C_4$ alkynyl, $C_2-C_4$ alkanoyl, $C_1-C_4$ alkoxy, $C_2-C_4$ alkenoxy, aryl, heteroaryl, aryl-$(C_1-C_4$ alkoxy) or heteroaryl-$(C_1-C_4$ alkoxy), in which "aryl" means phenyl optionally substituted by 1 to 3 substituents each independently selected from halo, $C_1-C_4$ alkyl, $C_1-C_4$ alkoxy, $C_1-C_4$ alkylthio, $C_1-C_4$ alkylsulphinyl and $C_1-C_4$ alkylsulphonyl, and in which "heteroaryl" means thienyl, furyl or pyridinyl all optionally substituted by 1 to 3 substituents each independently selected from halo, $C_1-C_4$ alkyl, $C_1-C_4$ alkoxy, $C_1-C_4$ alkylthio, $C_1-C_4$ alkylsulphinyl and $C_1-C_4$ alkylsulphonyl;

and $R_3$ is a $C_1-C_4$ alkyl group.

2. A compound as claimed in claim 1 in which $R^1$ is H, $C_1-C_4$ alkyl, $C_1-C_4$ alkoxy, $C_1-C_4$ alkylthio, $C_1-C_4$ alkylsulphinyl, phenylthio, phenylsulfinyl, benzoyl optionally substituted by halo, phenylsulfonyloxy optionally substituted by halo, or 1,2-benzisoxazol-3-yl.

3. A compound as claimed in claim 2 in which $R^1$ is H, benzoyl, 4-fluorobenzoyl, 4-fluorophenylsulfonyloxy, n-propylthio, n-propylsulfinyl, phenylthio, phenylsulfinyl, n-butyl, n-propyloxy, or 1,2-benzisoxazol- 3-yl.

4. A compound as claimed in claim 3 in which $R^1$ is n-propylthio.

5. A compound as claimed in claim 1 in which "alk" is methylene.

6. A compound as claimed in claim 1 in which $R^2$ is methoxy, ethoxy, allyloxy, benzyloxy, phenyl optionally substituted by 1 to 3 methoxy substituents, cyano, ethynyl, vinyl or acetyl.

7. A compound as claimed in claim 1 in which $R^3$ is methyl.

8. A veterinary composition comprising a compound of claim 1 or a non-toxic salt thereof as claimed in any one of the preceding claims, and a non-toxic diluent or carrier.

9. A composition as claimed in claim 8, which is in the form of a spot-on or pour-on formulation, or a parenteral formulation.

10. A method of combating helminths in an animal, which comprises applying to the skin of said animal an amount sufficient to exert an anthelmintic effect of a compound of the formula (I) or non-toxic salt thereof according to claim 1, whereby the compound or salt is absorbed by the animal through the skin.

* * * * *